(12) United States Patent
Hirama et al.

(10) Patent No.: US 7,834,006 B2
(45) Date of Patent: Nov. 16, 2010

(54) FUSED POLYCYCLIC COMPOUNDS

(75) Inventors: Ryusuke Hirama, Kawasaki (JP); Hideyuki Tanaka, Kawasaki (JP); Seiji Niwa, Kawasaki (JP); Akiyo Yamazaki, Kawasaki (JP); Takao Ikenoue, Kawasaki (JP); Koji Ohsumi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 1023 days.

(21) Appl. No.: 11/486,213

(22) Filed: Jul. 14, 2006

(65) Prior Publication Data

US 2006/0258637 A1 Nov. 16, 2006

Related U.S. Application Data

(63) Continuation of application No. PCT/JP2005/000348, filed on Jan. 14, 2005.

(30) Foreign Application Priority Data

Jan. 14, 2004 (JP) .............................. 2004-007179

(51) Int. Cl.
- A61P 3/04 (2006.01)
- A61P 3/10 (2006.01)
- A61P 9/10 (2006.01)
- A61P 13/12 (2006.01)
- A61P 25/02 (2006.01)
- A61P 43/00 (2006.01)
- A61K 31/551 (2006.01)
- C07D 487/04 (2006.01)

(52) U.S. Cl. .................. 514/221; 540/567; 540/568

(58) Field of Classification Search ............... 514/221; 540/567, 568

See application file for complete search history.

(56) References Cited

U.S. PATENT DOCUMENTS

| 2004/0048847 | A1 | 3/2004 | Iino et al. |
| 2005/0272641 | A1 | 12/2005 | Ikenoue et al. |
| 2006/0189597 | A1 | 8/2006 | Iino et al. |
| 2006/0194789 | A1 | 8/2006 | Hirama et al. |

FOREIGN PATENT DOCUMENTS

| JP | 2004-10523 | 1/2004 |
| WO | WO 02/44180 | 6/2002 |
| WO | WO 03/004495 | 1/2003 |
| WO | WO 2005/042536 | 5/2005 |

OTHER PUBLICATIONS

Simon Y.M. Chooi, et al., Tetrahedron: Asymmetry, vol. 2, No. 10, pp. 981-982 (1991).
Dawei Ma, et al., Tetrahedron: Asymmetry, vol. 7, No. 8. pp. 2365-2370 (1996).
Paul N. Devine et al., Tetrahedron Letters, vol. 32, No. 7, pp. 883-886 (1991).
Andreas Scheurer et al., Tetrahedron: Asymmetry 10 (1999) 3559-3570.
Ian A. Simpson et al., Annual Review of Biochemistry vol. 55, pp. 1059-1089 (1986).

*Primary Examiner*—Brenda L Coleman
(74) *Attorney, Agent, or Firm*—Oblon, Spivak, McClelland, Maier & Neustadt. L.L.P.

(57) ABSTRACT

The following fused polycyclic compound, analogues thereof or pharmaceutically acceptable salts thereof have an effect of increasing the sugar-transporting capacity and an effect of lowering the blood glucose level and, therefore, they are useful for preventing and/or treating diabetes and the like.

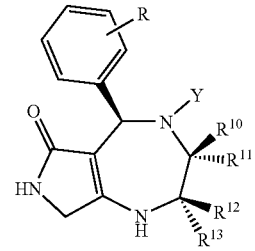

wherein R is a methoxy group, Y is a (2-thiazolyl)-2-ethyl-carbonyl group, $R^{10}$ and $R^{13}$ are hydrogen atoms, and $R^{11}$ and $R^{12}$ are methyl groups.

20 Claims, No Drawings

FUSED POLYCYCLIC COMPOUNDS

CROSS REFERENCES TO RELATED APPLICATIONS

This application is a continuation of International Patent Application No. PCT/JP05/00348, filed on Jan. 14, 2005, and claims priority to Japanese Patent Application No. 2004-007179, filed on Jan. 14, 2004.

TECHNICAL FIELD OF THE INVENTION

The present invention relates to new fused polycyclic compounds and drugs for treating diabetes which have the compounds as an active ingredient.

BACKGROUND OF THE INVENTION

Drug therapy of Type II diabetes is positioned as a treatment for patients whose conditions are not sufficiently improved by dietary therapy or exercise therapy. Up to now, agents have been developed such as preparations with insulin that is an endogenous hormone controlling hypoglycemic actions, or oral hypoglycemic agents having actions such as insulin secretagogue action or peripheral insulin sensitizing action. At present, it is the mainstream method of drug therapy of Type II diabetes that blood glucose is precisely controlled by using oral hypoglycemic agents. However, in case that sufficient insulin actions cannot be obtained to improve hyperglycemia by using such agents, insulin therapy is applied as a main method. On the other hand, to Type I diabetes, administration of insulin therapy is the only treatment because such patients' insulin secretion ability is extinct.

Thus, though the insulin therapy is used as an important treatment method, there are problems such as procedure complication and need of patient education because it is injection solutions. Accordingly, improvement in the administration method is strongly desired from the aspect of improvement in compliance. Recent years, several insulin administration methods by various non-injection preparations to replace injection solutions have been developed and tried, but they are not led to practical use because of the problems such as the poor absorption efficiency and unstable absorption thereof.

As one of the main hypoglycemic actions of insulin, insulin has the action which increases the sugar-transporting capacity of peripheral cells, makes sugars in the blood take in the peripheral cells, and, as a result, lowers the blood glucose level. Thus, if new oral medicaments are found such as those lowering the blood glucose level by an effect of increasing the sugar-transporting capacity of peripheral cells, it is expected to become a promising treatment for diabetic diseases. For example, the compounds described in Patent Literature 1 are known.

[Patent Literature 1] WO 02/44180

DISCLOSURE OF THE INVENTION

The object of the present invention is to develop and provide a drug for treating diabetes which has high medicinal properties and few side-effects.

The further object of the present invention is to provide an agent having an effect of increasing the sugar-transporting capacity.

The additional object of the present invention is to provide a hypoglycemic agent.

The further additional object of the present invention is to provide a drug for preventing and/or treating diabetes, diabetic peripheral neuropathy, diabetic nephropathy, diabetic retinopathy, diabetic macroangiopathy, impaired glucose tolerance or obesity.

The further additional object of the present invention is to provide a new fused polycyclic compound having a heterocyclic ring(s).

The further additional object of the present invention is to provide a pharmaceutical composition.

The inventors thoroughly examined compounds useful as drugs for treating diabetes, which have a strong effect of increasing the sugar-transporting capacity, and found that specific fused polycyclic compounds have such effects. The present invention has been completed based of this finding.

Namely, the present invention provides the following inventions.

(1) A fused polycyclic compound of the following formula (I) or pharmaceutically acceptable salts thereof:

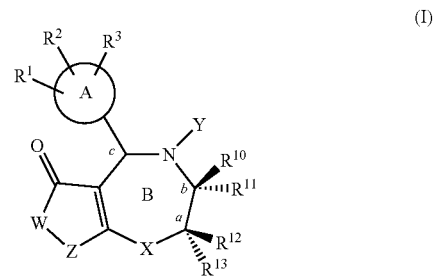

(I)

wherein A represents an aromatic cyclic group, heterocyclic group or aliphatic cyclic group; $R^1$, $R^2$ and $R^3$ may be same or different from each other and each independently represent a hydrogen atom, halogen atom, hydroxyl group, mercapto group, alkoxy group, alkylthio group, alkylsulfonyl group, acyl group, acyloxy group, amino group, alkylamino group, carboxyl group, alkoxycarbonyl group, carbamoyl group, nitro group, cyano group, trifluoromethyl group, alkyl group which may have a substituent(s), alkenyl group which may have a substituent(s), alkynyl group which may have a substituent(s), aryl group which may have a substituent(s), heteroaryl group which may have a substituent(s), benzyloxy group which may have a substituent(s), aryloxy group which may have a substituent(s), heteroaryloxy group which may have a substituent(s), arylamino group which may have a substituent(s), arylvinyl group which may have a substituent(s) or arylethynyl group which may have a substituent(s); —X— and —Z— may be same or different from each other and each independently represent —O—, —NH—, —NR$^6$—, —S—, —SO—, —SO$_2$—, —CH$_2$—, —CR$^4$R$^5$— or —CO—, wherein $R^6$ represents a lower alkyl group which may have a substituent(s), acyl group which may have a substituent(s), alkoxycarbonyl group which may have a substituent(s), carbamoyl group which may have a substituent(s) or sulfonyl group which may have a substituent(s), $R^4$ and $R^5$ may be same or different from each other and each independently represent a hydrogen atom, halogen atom, hydroxyl group, alkyl group, mercapto group, alkoxy group, alkylthio group, alkylsulfonyl group, acyl group, acyloxy group, amino group, alkylamino group, carboxyl group, alkoxycarbonyl group, carbamoyl group, nitro group, cyano group or trifluoromethyl group; —W— represents —NR$^9$—, —O— or —CR$^7$R$^8$—, wherein $R^9$ represents a hydrogen atom, lower alkyl group which may have a substituent(s) or aryl group which may have a substituent(s), $R^7$ and $R^8$ may be same or different from each other and each independently represent a hydrogen atom, halogen atom, hydroxyl group, alkyl group, mercapto group, alkoxy group, alkylthio group, alkylsulfonyl group, acyl group, acyloxy group, amino group, alkylamino group, carboxyl group, alkoxycarbonyl group, carbamoyl group, nitro group, cyano group or trifluoromethyl group; Y represents a lower alkyl group which may have a substituent(s), acyl group which may have a substituent(s), alkoxycarbonyl group which may have a substituent(s), carbamoyl group which may have a substituent(s) or sulfonyl group which may have a substituent(s); $R^{10}$, $R^{11}$, $R^{12}$ and $R^{13}$ may be same or different from each other and each independently represent a hydrogen atom, halogen atom, lower alkyl group which may have a substituent(s), lower alkenyl group which may have a substituent(s), lower alkynyl group which may have a substituent(s), aryl group which may have a substituent(s), heteroaryl group which may have a substituent(s), carboxyl group, alkoxycarbonyl group, carbamoyl group or cyano group; and a, b and c represent a position of a carbon atom, respectively; with the proviso that (i) the above substituent(s) is selected from the group consisting of a halogen atom, hydroxyl group, alkyl group, mercapto group, alkoxy group, alkylthio group, alkylsulfonyl group, acyl group, acyloxy group, amino group, alkylamino group, carboxyl group, alkoxycarbonyl group, carbamoyl group, nitro group, cyano group, trifluoromethyl group, aryl group and heteroaryl group; and (ii) two or more of $R^{10}$, $R^{11}$, $R^{12}$ and $R^{13}$ do not form a ring together.

(2) The fused polycyclic compound or pharmaceutically acceptable salts thereof according to above (1), wherein A represents an aromatic cyclic group or heterocyclic group; —X— represents —NH— or —$NR^6$—; —Z— represents —$CH_2$— or —$CR^4R^5$—; —W— represents —$NR^9$—; Y represents an acyl group which may have a substituent(s), alkoxycarbonyl group which may have a substituent(s) or carbamoyl group which may have a substituent(s); either one or both of $R^{10}$ and $R^{11}$ is a hydrogen atom; and either one or both of $R^{12}$ and $R^{13}$ is a hydrogen atom.

(3) The fused polycyclic compound or pharmaceutically acceptable salts thereof according to above (2), wherein Y is an acyl group which may have a substituent(s) and represented by the following formula (II):

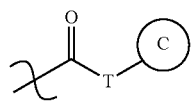

(II)

wherein two carbon atoms in T may have a double bond or triple bond, part of the carbon atom(s) in the group may be substituted with an oxygen, sulfur or nitrogen atom, and T represents an alkylene group having 1 to 7 carbon atoms; and C represents an aromatic cyclic group or heterocyclic group.

(4) The fused polycyclic compound or pharmaceutically acceptable salts thereof according to above (3), wherein C represents a furyl group which may have a substituent(s), thienyl group which may have a substituent(s), oxazolyl group which may have a substituent(s), isoxazolyl group which may have a substituent(s), thiazolyl group which may have a substituent(s), oxadiazolyl group which may have a substituent(s), thiadiazolyl group which may have a substituent(s), pyridyl group which may have a substituent(s), piperidyl group which may have a substituent(s), pyridonyl group which may have a substituent(s), pyridazinyl group which may have a substituent(s), pyrimidinyl group which may have a substituent(s), imidazolyl group which may have a substituent(s), or 4-oxothiazolidine-2-thionyl group which may have a substituent(s); and -T- represents —$CH_2$— or —$CH_2CH_2$—.

(5) The fused polycyclic compound or pharmaceutically acceptable salts thereof according to above (4), wherein C represents a furyl group, thienyl group, oxazolyl group, isoxazolyl group, thiazolyl group, oxadiazolyl group, pyridyl group, piperidyl group, pyridazinyl group, or pyrimidinyl group.

(6) The fused polycyclic compound or pharmaceutically acceptable salts thereof according to above (2), wherein Y represents an unsubstituted acyl group or acyl group which has an alkyl group(s) with 1 to 6 carbon atoms having a hydroxyl group as a substituent.

(7) The fused polycyclic compound or pharmaceutically acceptable salts thereof according to above (2), wherein A is a phenyl group substituted upward on paper to Ring B; —X— represents —NH— or —NMe—; W is —NH—; both $R^{10}$ and $R^{13}$ are hydrogen atoms; and $R^{11}$ and $R^{12}$ may be same or different from each other and each independently represent a hydrogen atom, lower alkyl group which may have a substituent(s), lower alkenyl group which may have a substituent(s), or lower alkynyl group which may have a substituent(s).

(8) The fused polycyclic compound or pharmaceutically acceptable salts thereof according to above (2), wherein all of $R^1$, $R^2$ and $R^3$ are hydrogen atoms, or two in $R^1$, $R^2$ and $R^3$ are hydrogen atoms and the rest is an alkoxy group, alkylthio group, alkylsulfonyl group, acyl group, acyloxy group, amino group, alkylamino group, alkoxycarbonyl group, carbamoyl group, trifluoromethyl group, alkyl group which may have a substituent(s), alkenyl group which may have a substituent(s), or alkynyl group which may have a substituent(s).

(9) The fused polycyclic compound or pharmaceutically acceptable salts thereof according to above (8), wherein all of $R^1$, $R^2$ and $R^3$ are hydrogen atoms, or two in $R^1$, $R^2$ and $R^3$ are hydrogen atoms and the rest is an alkoxy group having 1 to 18 carbon atoms, alkylthio group having 1 to 12 carbon atoms, alkylsulfonyl group having 1 to 12 carbon atoms, trifluoromethyl group, or alkyl group having 1 to 18 carbon atoms.

(10) The fused polycyclic compound or pharmaceutically acceptable salts thereof according to above (7), wherein $R^{11}$ and $R^{12}$ may be same or different from each other and each independently represent a lower alkyl group which may have a substituent(s), lower alkenyl group which may have a substituent(s), or lower alkynyl group which may have a substituent(s).

(11) The fused polycyclic compound or pharmaceutically acceptable salts thereof according to above (10), wherein $R^{11}$ and $R^{12}$ may be same or different from each other and each independently represent a lower alkyl group which may have a substituent(s).

(12) An agent for increasing the sugar-transporting capacity, which comprises the fused polycyclic compound or pharmaceutically acceptable salts thereof according to any one of above (1) to (11) as an active ingredient.

(13) A hypoglycemic agent; an agent for preventing and/or treating diabetes, diabetic peripheral neuropathy, diabetic nephropathy, diabetic retinopathy, diabetic macroangiopathy, impaired glucose tolerance, or obesity; or a pharmaceutical composition comprising the fused polycyclic compound or pharmaceutically acceptable salts thereof according to any one of above (1) to (11) as an active ingredient.

BEST MODE FOR CARRYING OUT THE INVENTION

The effect of increasing the sugar-transporting capacity in the present invention indicates the action which increases the sugar-transporting capacity via biological membranes. It may act on the sugar transportation from outside to inside of the biological membranes or that from inside to outside of the biological membranes. More concretely, for example, there is an insulin action, that is, the effect of increasing the glucose-transporting in and to adipose cells and muscle cells.

Sugars in the "sugar-transporting" indicate pentoses or hexoses that exist in vivo. Examples thereof include glucose, mannose, arabinose, galactose, and fructose. Glucose is preferable among them.

A lower alkyl group represents a linear- or branched-chain or cyclic alkyl group having 1 to 6 carbon atoms, preferably 1 to 4 carbon atoms and more preferably 1 to 3 carbon atoms. For example, it includes a methyl group, ethyl group, n-propyl group, n-butyl group, n-pentyl group, n-hexyl group, isopropyl group, isobutyl group, sec-butyl group, tert-butyl group, isopentyl group, tert-pentyl group, neopentyl group, 2-pentyl group, 3-pentyl group, n-hexyl group, 2-hexyl group, cyclopropyl group, cyclobutyl group, cyclopentyl group and cyclohexyl group. A methyl group and ethyl group are preferable among them.

An aryl group represents a mono-, bi- or tri-cyclic aromatic substituent(s) composed of carbon atoms and preferably a mono- or bi-cyclic aromatic substituent(s) composed of 5 to 12 carbon atoms. Examples thereof are a phenyl group, indenyl group, naphthyl group and fluorenyl group, and a phenyl group is preferable among them.

A halogen atom includes a fluorine atom, chlorine atom, bromine atom and iodine atom.

An alkyl group represents a linear- or branched-chain or cyclic alkyl group having 1 to 18 carbon atoms and preferably 1 to 12 carbon atoms. For example, it includes a methyl group, ethyl group, n-propyl group, n-butyl group, n-pentyl group, n-hexyl group, n-heptyl group, n-octyl group, n-nonyl group, n-decyl group, n-undecyl group, n-dodecyl group, isopropyl group, isobutyl group, sec-butyl group, tert-butyl group, isopentyl group, tert-pentyl group, neopentyl group, 2-pentyl group, 3-pentyl group, n-hexyl group, 2-hexyl group, tert-octyl group, cyclopropyl group, cyclobutyl group, cyclopentyl group, cyclohexyl group and 1-adamantyl group. An n-hexyl group, n-heptyl group, n-octyl group, n-nonyl group, n-decyl group, n-undecyl group, n-dodecyl group, isopropyl group, isobutyl group, sec-butyl group, tert-butyl group, isopentyl group, tert-pentyl group, neopentyl group, 2-pentyl group, 3-pentyl group, n-hexyl group, 2-hexyl group, tert-octyl group, cyclopropyl group, cyclobutyl group, cyclopentyl group, cyclohexyl group, 1-adamantyl group and the like are preferable, and an isopropyl group, tert-butyl group, tert-octyl group, 1-adamantyl group and the like are more preferable among them. Further, a lower alkyl group is also preferable.

An alkenyl group and alkynyl group include those having 2 to 18 carbon atoms, preferably 2 to 12 carbon atoms and more preferably 2 to 6 carbon atoms.

An alkoxy group represents an alkoxy group which has a linear- or branched-chain or cyclic alkyl group having 1 to 18 carbon atoms, preferably 1 to 12 carbon atoms and more preferably 1 to 6 carbon atoms. For example, it includes a methoxy group, ethoxy group, n-propoxy group, n-butoxy group, n-pentyloxy group, n-hexyloxy group, n-heptyloxy group, n-octyloxy group, n-nonyloxy group, n-decyloxy group, n-undecyloxy group, n-dodecyloxy group, isopropoxy group, isobutoxy group, sec-butoxy group, tert-butoxy group, cyclopropyloxy group, cyclobutoxy group, cyclopentyloxy group, cyclohexyloxy group, cycloheptyloxy group, 2-cyclohexylethoxy group, 1-adamantyloxy group, 2-adamantyloxy group, 1-adamantylmethyloxy group, 2-(1-adamantyl)ethyloxy group and trifluoromethoxy group. Among them, a methoxy group, ethoxy group, n-propoxy group, isopropoxy group, n-butoxy group, tert-butoxy group, n-pentyloxy group and n-hexyloxy group are preferable.

Further the alkoxy group includes the alkoxy group substituted with a fluorine atom(s). More concretely, it includes a fluoromethyloxy group, trifluoromethyloxy group, trifluoroethyloxy group, and pentafluoroethyloxy group. A trifluoromethyloxy group is preferable among them.

An alkylthio group represents an alkylthio group which has a linear- or branched-chain or cyclic alkyl group having 1 to 12 carbon atoms and preferably 1 to 6 carbon atoms. For example, it includes a methylthio group, ethylthio group, n-propylthio group, isopropylthio group, n-butylthio group, isobutylthio group, sec-butylthio group, tert-butylthio group, cyclopropylthio group, cyclobutylthio group, cyclopentylthio group and cyclobutylthio group.

An alkylsulfonyl group represents an alkylsulfonyl group which has a linear- or branched-chain or cyclic alkyl group having 1 to 12 carbon atoms and preferably 1 to 6 carbon atoms. For example, it includes a methanesulfonyl group, ethanesulfonyl group, propanesulfonyl group, butanesulfonyl group, pentanesulfonyl group, hexanesulfonyl group, heptanesulfonyl group, octanesulfonyl group, nonanesulfonyl group, decanesulfonyl group, undecanesulfonyl group and dodecanesulfonyl group.

An acyl group represents a formyl group, an acyl group which has a linear- or branched-chain or cyclic alkyl group having 1 to 6 carbon atoms and preferably 1 to 4 carbon atoms, an acyl group which has a linear- or branched-chain or cyclic alkenyl group having 1 to 6 carbon atoms and preferably 1 to 4 carbon atoms, an acyl group which has a linear- or branched-chain or cyclic alkynyl group having 1 to 6 carbon atoms, or an acyl group which has an aryl group that may be substituted. Examples thereof are a formyl group, acetyl group, propionyl group, butyryl group, isobutyryl group, valeryl group, isovaleryl group, pivaloyl group, hexanoyl group, acryloyl group, metacryloyl group, crotonoyl group, isocrotonoyl group, benzoyl group and naphthoyl group. Further, it also includes the acyl group which may have a substituent(s), indicated as the above formula (II). The alkyl group in the acyl group may have a hydroxy group or halogen group.

An acyloxy group represents a formyloxy group, an acyloxy group which has a linear- or branched-chain or cyclic alkyl group having 1 to 6 carbon atoms, or an acyloxy group which has an aryl group that may be substituted. For example, it includes a formyloxy group, acetyloxy group, propionyloxy group, butyryloxy group, isobutyryloxy group, valeryloxy group, isovaleryloxy group, pivaloyloxy group, hexanoyloxy group, acryloyloxy group, metacryloyloxy group, crotonoyloxy group, isocrotonoyloxy group, benzoyloxy group and naphthoyloxy group.

Further, the acyloxy group also includes the oxy group substituted with an acyl group(s) which may have a substituent(s), indicated as the above formula (II).

An alkylamino group represents an amino group which is monosubstituted or disubstituted with an alkyl group(s), and examples of the alkyl group(s) are the same as those mentioned in the above "alkyl group." Concretely, they include a methylamino group, ethylamino group, propylamino group, isopropylamino group, dimethylamino group, diethylamino group, dipropylamino group, diisopropylamino group and methylethylamino group.

An alkoxycarbonyl group represents an alkoxycarbonyl group which has a linear- or branched-chain or cyclic alkyl group having 1 to 8 carbon atoms. Examples thereof are a methoxycarbonyl group, ethoxycarbonyl group, propoxycarbonyl group, isopropoxycarbonyl group, n-butoxycarbonyl group, isobutoxycarbonyl group, sec-butoxycarbonyl group, tert-butoxycarbonyl group and benzyloxycarbonyl group.

A carbamoyl group represents a carbamoyl group which may have a linear- or branched-chain or cyclic alkyl group having 1 to 6 carbon atoms on a nitrogen. For example, it includes a carbamoyl group, N-methylcarbamoyl group, N-ethylcarbamoyl group, N,N-dimethylcarbamoyl group, N-pyrrolidylcarbonyl group, N-piperidylcarbonyl group and N-morpholinylcarbonyl group.

A sulfonyl group represents a sulfonyl group which may have a linear- or branched-chain or cyclic alkyl group having 1 to 6 carbon atoms on a sulfur atom. For example, it includes a methylsulfonyl group, ethylsulfonyl group, propylsulfonyl group and butylsulfonyl group.

An aromatic ring represents a mono-, bi- or tri-cyclic aromatic ring composed of carbon atoms and preferably a monocyclic or bicyclic aromatic ring. For example, it includes a benzene ring, naphthalene ring, indene ring and fluorene ring, and a benzene ring and naphthalene ring are preferable.

A heterocyclic ring represents a heterocyclic ring consisting of 1 to 3 ring(s) each comprising 5 to 7 members of carbon and nitrogen, oxygen, sulfur or the like. For example, it includes a pyridine ring, dihydropyran ring, pyridazine ring, pyrimidine ring, pyrazine ring, pyrrole ring, furan ring, thiophene ring, oxazole ring, isooxazole ring, pyrazole ring, imidazole ring, thiazole ring, isothiazole ring, thiadiazole ring, pyrrolidine ring, piperidine ring, piperazine ring, indole ring, isoindole ring, benzofuran ring, isobenzofuran ring, benzothiophene ring, benzopyrazole ring, benzoimidazole ring, benzooxazole ring, benzothiazole ring, purine ring, pyrazolopyridine ring, quinoline ring, isoquinoline ring, naphthyridine ring, quinazoline ring, benzodiazepine ring, carbazole ring and dibenzofuran ring. A pyridine ring, pyrimidine ring, pyridazine ring, pyrimidine ring, furan ring and thiophene ring are preferable among them.

An aliphatic ring represents a monocyclic or bicyclic aliphatic ring which is composed of carbon atoms. For example, it includes a cyclopropane ring, cyclobutane ring, cyclopentane ring, cyclohexane ring, cycloheptane ring, cyclooctane ring, decalin rings and norbornane ring, and cyclohexane ring is preferable. It preferably has 3 to 8 carbon atoms.

An heteroaryl group represents an aromatic heterocyclic substituent consisting of 1 to 3 ring(s) each comprising 5 to 7 members of carbon and nitrogen, oxygen, sulfur or the like. For example, it includes a pyridyl group, pyridazinyl group, pyrimidinyl group, pyrazinyl group, pyrrolyl group, furanyl group, thienyl group, oxazolyl group, isoxazolyl group, pyrazolyl group, imidazolyl group, thiazolyl group, isothiazolyl group, thiadiazolyl group, indolyl group, isoindolyl group, benzofuryl group, isobenzofuryl group, benzothienyl group, benzopyrazolyl group, benzoimidazolyl group, benzoxazolyl group, benzothiazolyl group, quinolyl group, isoquinolyl group, naphthyridinyl group and quinazolyl group. A 2-pyridyl group, 3-pyridyl group, 4-pyridyl group and 1-pyrazolyl group are preferable among them.

An aryloxy group is an aryloxy group having an aryl group on an oxygen atom, and examples of the aryl group are the same as those mentioned in the above "aryl group." Concretely, it includes a phenoxy group, 1-naphthyloxy group and 2-naphthyloxy group.

A heteroaryloxy group is a heteroaryloxy group having a heteroaryl group on an oxygen atom, and examples of the heteroaryl group are the same as those mentioned in the above "heteroaryl group." Concretely, it includes a 2-pyridyloxy group, 3-pyridyloxy group, 4-pyridyloxy group and 2-pyrimidinyloxy group.

An arylamino group is an arylamino group having an aryl group(s) on a nitrogen atom and examples of the aryl group(s) are the same as those mentioned in the above "aryl group." Concretely, it includes a phenylamino group, 1-naphthylamino group and 2-naphthylamino group.

An arylvinyl group is a vinyl group of which the first position or the second position is substituted with an aryl group(s), and examples of the aryl group(s) are the same as those mentioned in the above "aryl group." Concretely, it includes a 1-phenylvinyl group and 2-phenylvinyl group.

An arylethynyl group is an ethynyl group of which the second position is substituted with an aryl group(s), and examples of the aryl group(s) are the same as those mentioned in the above "aryl group." Concretely, it includes a phenylethynyl group.

The term "which may have a substituent(s)" includes both cases in which a group does not have any substituents and in which a group has a substituent(s). In case that a group has a substituent(s), at least one or more thereof are substituted with the substituent(s) mentioned in the above (I). The substituent(s) may be same or different from each other, and the position and number thereof are optional and not particularly limited.

Further, in the present invention, the fused polycyclic compound of the formula (I) according to claim 1 or pharmaceutically acceptable salts thereof are preferably those mentioned below.

$R^1$, $R^2$ and $R^3$ are preferably a hydrogen atom, halogen atom, hydroxyl group, alkyl group, alkoxy group, alkylthio group, acyl group, acyloxy group, amino group, alkoxycarbonyl group, carbamoyl group, nitro group, cyano group, trifluoromethyl group, trifluoromethoxy group, aryl group which may have a substituent(s), heteroaryl group which may have a substituent(s), benzyloxy group, aryloxy group which may have a substituent(s) or arylethynyl group which may have a substituent(s). More preferable ones are a hydrogen atom, halogen atom, hydroxyl group, methyl group, ethyl group, propyl group, isopropyl group, cyclopropyl group, methoxy group, ethoxy group, methylthio group, ethylthio group, n-propoxy group, isopropoxy group, trifluoromethyl group and trifluoromethoxy group.

—X— is preferably —NH—, —NR$^6$— wherein $R^6$ represents a lower alkyl group, —O—, —S— or —CH$_2$—. —NH— or —NMe- is more preferable among them. —NH— is particularly preferable among them.

—Y— is preferably an acyl group which may have a substituent(s), alkoxycarbonyl group which may have a substituent(s), or carbamoyl group which may have a substituent(s). More preferable ones are an acetyl group, propanoyl group, butanoyl group, hydroxyacetyl group, methoxycarbonyl group, ethoxycarbonyl group, ethylcarbamoyl group and the acyl group of the formula (II). Besides, an acetyl group, propanoyl group, hydroxyacetyl group, 3-(2-thiazolyl)propanoyl group, or 3-(2-pyridyl)propanoyl group is further more preferable.

—Z— is preferably —NH— or —CR$^4$R$^5$— wherein $R^4$ and $R^5$ may be same or different from each other and each independently represent a hydrogen atom or a lower alkyl group which may have a substituent(s), and —CH$_2$— is more preferable.

—W— is preferably —NH—, —NR$^9$— wherein R$^9$ represents a lower alkyl group, or —CH$_2$—, and —NH— is more preferable.

A is preferably an aromatic cyclic group or a heterocyclic group. A benzene ring, pyridine ring, pyrimidine ring, and thiophene ring are more preferable, and a benzene ring is further more preferable.

As for the configuration of a carbon atom in the position c, it is preferable that A is substituted upward or downward on paper to B, and it is more preferable that A is substituted upward on paper to B.

Ring C is preferably a furan which may have a substituent(s), thiophene which may have a substituent(s), oxazole which may have a substituent(s), isoxazole which may have a substituent(s), thiazole which may have a substituent(s), oxadiazole which may have a substituent(s), thiadiazole which may have a substituent(s), pyridine which may have a substituent(s), piperidine which may have a substituent(s), pyridone which may have a substituent(s), pyridazine which may have a substituent(s), pyrimidine which may have a substituent(s), imidazole which may have a substituent(s), or 4-oxothiazolidine-2-thione which may have a substituent(s). A pyridine which may have a substituent(s) or thiadiazole which may have a substituent(s) are more preferable among them. Particularly, thiazole and pyridine are more preferable.

-T- is preferably a bond consisting of one or two atom(s). —CH$_2$— or —CH$_2$CH$_2$— is more preferable, and —CH$_2$CH$_2$— is particularly preferable.

R$^{10}$, R$^{11}$, R$^{12}$ and R$^{13}$ may be same or different from each other and preferably each independently represent a hydrogen atom, lower alkyl group which may have a substituent(s), alkynyl group which may have a substituent(s), or alkenyl group which may have a substituent(s). It is further more preferable that R$^{10}$ and R$^{13}$ are hydrogen atoms, and R$^{11}$ and R$^{12}$ may be same or different from each other and each independently represent a hydrogen atom, methyl group, ethyl group, n-propyl group, isopropyl group, cyclopropyl group, monofluoromethyl group, monofluoroethyl group, or trifluoromethyl group.

It is particularly preferable that R$^{10}$ and R$^{13}$ are hydrogen atoms.

It is particularly preferable that R$^{11}$ and R$^{12}$ are methyl groups or ethyl groups.

The pharmaceutically acceptable salts include, for example, in the case of the compounds of the present invention, which are sufficiently acidic, ammonium salts thereof, alkali metal salts (such as sodium salts and potassium salts, as preferable examples), alkaline earth metal salts (such as calcium salts and magnesium salts, as preferable examples); as salts of an organic base, for example, dicyclohexylamine salts, benzathine salts, N-methyl-D-glucan salts, hydramine salts, and salts of amino acids such as arginine and lysine. Further, in the case of the compounds of the present invention, which are sufficiently basic, the salts include acid addition salts thereof, such as those with inorganic acids, e.g. hydrochloric acid, sulfuric acid, nitric acid and phosphoric acid; or those with organic acids, e.g. acetic acid, lactic acid, citric acid, tartaric acid, maleic acid, fumaric acid and monomethyl sulfate. In some cases, they may be wet salts or hydrates.

The present invention includes all isomers such as optical isomers and geometric isomers, hydrates, solvates or crystal forms.

The compound of the present invention can be synthesized by using or applying the method described in WO02/44180.

For example, in the compound (I) of the present invention, a compound (IX) wherein —Z— is —CH$_2$—; and —X— and —W— are —NH— can be synthesized as mentioned below. Namely, a diamine (III) and a compound (IV) are fused to form a compound (V); and then the compound (V) is fused with an aldehyde (VI) to form a compound (VII). The compound (VII) is led to a compound (VIII) by alkylation or acylation in accordance with known methods. In case that R$^{14}$ is not hydrogen, the lactam part thereof is deprotected to be able to obtain a compound (IX).

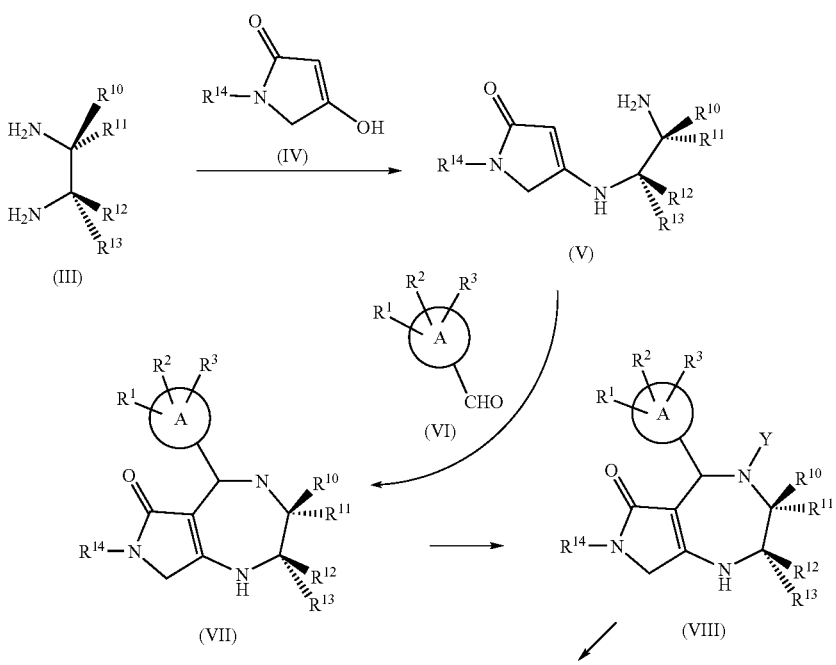

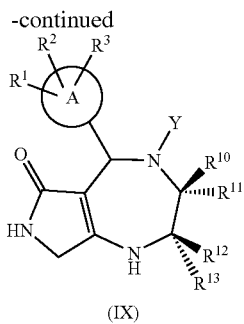

(IX)

R14 represents a hydrogen atom or a protective group such as Cbz group, Boc group and Fmoc group.

Further, in the compound (I) of the present invention, a compound (XI) wherein —Z— is —CH$_2$—; —W— is —NH—; and —X— is —NR$^6$— wherein R$^6$ is an alkyl group which may have a substituent(s) can be synthesized as mentioned below. Namely, an alkylating agent such as alkyl halide is acted on the compound (VIII) under the existence of a base such as sodium hydride to form a compound (X). Then, the lactam part thereof is deprotected to be able to obtain a compound (XI).

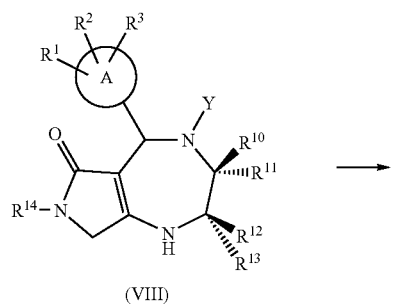

(VIII)

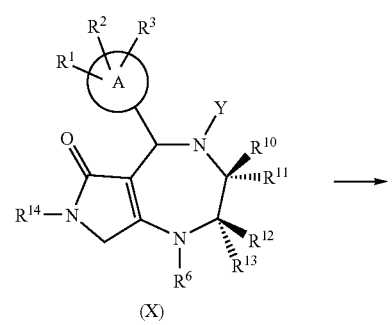

(X)

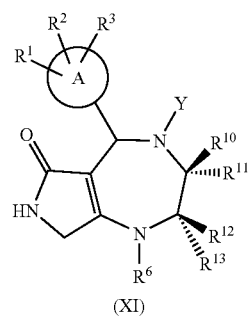

(XI)

R14 represents a protective group such as Cbz group, Boc group and Fmoc group.

As the diamine (III) used as a raw ingredient, known diamines can be used without change, or those synthesized by the method described in a literature (Tetrahedron Asymmetry 1991, 2(10), 981-982) or those easily led from known diols and dicarboxylic derivatives by the known methods can be used. The compound (IV) can be synthesized by the method described in a literature (Tetrahedron Asymmetry 1996, 7(8), 2365-2370) or that described in WO02/44180.

The compounds of the present invention other than those mentioned above can also be synthesized by applying the above reactions.

Meanwhile, the compounds of the present invention obtained by the above methods can be purified with methods usually used in organic syntheses, such as extraction, distillation, crystallization and column chromatography.

The obtained compounds of the present invention have an effect of increasing the sugar-transporting capacity as mentioned below, and are useful for treating patients, taking advantage of this action. Namely, since an effect of increasing the sugar-transporting capacity lowers the blood glucose level, the compounds of the present invention are useful as drugs preventing and/or treating diabetes, diabetic peripheral neuropathy, diabetic nephropathy, diabetic retinopathy, diabetic macroangiopathy, impaired glucose tolerance or obesity.

When using the compounds of the present invention as the drugs preventing and/or treating diabetes, diabetic peripheral neuropathy, diabetic nephropathy, diabetic retinopathy, diabetic macroangiopathy, impaired glucose tolerance or obesity, they can be administered orally, intravenously, or transdermally. Though the dosage differs depending on a patient's symptom, age and administration method, it is usually 0.001 to 1000 mg/kg/day.

The compounds of the present invention can be formulated into a pharmaceutical preparation by ordinary methods. The dosage forms are, for example, injection solvents, tablets, granules, subtle granules, powders, capsules, cream pharmaceuticals and suppositories. The preparation carriers include such as lactose, glucose, D-mannitol, starch, crystalline cellulose, calcium carbonate, kaolin, starch, gelatin, hydroxypropyl cellulose, hydroxypropyl methyl cellulose, polyvinylpyrrolidone, ethanol, carboxy methyl cellulose, carboxy methyl cellulose calcium salts, magnesium stearate, talc, acetyl cellulose, sucrose, titanium oxide, benzoic acid, p-hydroxybenzoate ester, sodium dehydroacetate, gum arabic, tragacanth, methyl cellulose, egg yolk, surfactants, sucrose, simple syrup, citric acid, distilled water, ethanol, glycerin, propylene glycols, macrogol, monobasic sodium phosphate, dibasic sodium phosphate, sodium phosphate, glucose, sodium chloride, phenol, thimerosal, p-hydroxybenzoate ester and acid sodium sulfite. They are used by being mixed with the compounds of the present invention depending on the dosage forms.

Further, the content of the active ingredient of the present invention in the preparation of the present invention significantly varies depending on the dosage forms and is not particularly limited. Generally, the content is about 0.01 to 100 wt %, and preferably 1 to 100 wt % to a total amount of compositions.

The compounds of the present invention have an effect of increasing the sugar-transporting capacity, and are useful for treating the diabetic diseases. Namely, since an effect of increasing the sugar-transporting capacity lowers the blood glucose, the compounds of the present invention are useful as drugs preventing and/or treating diabetes, diabetic peripheral neuropathy, diabetic nephropathy, diabetic retinopathy, diabetic macroangiopathy, impaired glucose tolerance or obesity.

Next, Examples will further illustrate the present invention. They only explain the present invention and do not particularly limit the invention.

Example 1

(Process 1)

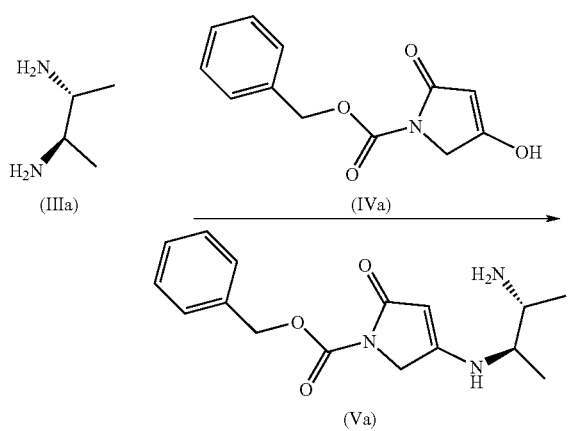

464 mg (5.27 mmol) of (R,R)-2,3-diaminobutan (IIIa) and 1.23 g (5.27 mmol) of a compound (IVa) synthesized by the method described in a literature (Tetrahedron Asymmetry 1996, 7(8), 2365-2370) were fused and purified in accordance with the method described in WO02/44180 to obtain 1.00 g of a Process 1 compound (Va) (yield 63%) as a pale yellow solid substance.

1H-NMR (300 MHz, CDCl3) δ=1.07 (3H, d, J=6.3 Hz), 1.14 (3H, d, J=6.6 Hz), 2.97-3.17 (2H, m), 4.21 (1H, d, J=18.0 Hz), 4.27 (1H, d, J=18.0 Hz), 4.67 (1H, s), 5.24 (2H, s), 5.82 (1H, d, J=7.5 Hz), 7.25-7.44 (5H, m). MS(ESI) m/z 304 (M+H)+.

(Process 2)

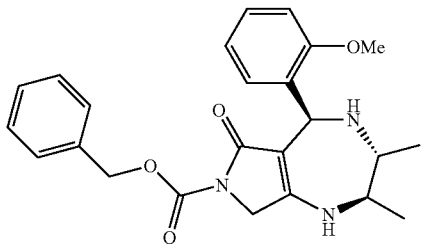

441 mg (1.46 mmol) of the Process 1 compound (Va) and 218 mg (1.60 mmol) of o-anisaldehyde were fused and purified in accordance with the method described in WO02/44180 to obtain 426 mg of a Process 2 compound (VIIa) (yield 69%)

1H-NMR (300 MHz, CDCl3) δ=0.86 (3H, d, J=6.6 Hz), 1.05 (3H, d, J=6.6 Hz), 2.43-2.56 (1H, m), 3.22-3.36 (1H, m), 3.86 (3H, s), 4.21 (1H, d, J=18.0 Hz), 4.28 (1H, d, J=18.0 Hz), 4.55 (1H, s), 5.33 (1H, d, J=13.5 Hz), 5.39 (1H, d, J=13.5 Hz), 6.78-6.93 (3H, m), 7.16-7.45 (7H, m). MS(ESI) m/z 422 (M+H)+.

(Process 3)

0.2 mL of acetic anhydride was added to a solution consisting of 64 mg (0.152 mmol) of the Process 2 compound (VIIa) and 2 mL of pyridine and stirred for 15 hours. The reaction solution was condensed under reduced pressure and separated by the ordinary separation treatment. Then, the organic layer thereof was dried on anhydrous sodium sulfate and condensed under reduced pressure. The obtained oily substance was dissolved in methanol, and the catalytic reduction with hydrogen was conducted thereto with 10% palladium carbon under normal pressure. Then, the reaction substance was purified by silica gel column chromatography to obtain a compound 1.

The structural formula of the compound 1 and data on the compound are shown in the following Table 1. In this regard, the symbols in the Table are as follows: No.: Example/Compound No., R: a substituent on a benzene ring, D: data on the compound, MS:ESI-MS m/z, N1: 1H-NMR (DMSO-d6, TMS internal standard, δ ppm). The number located in front of a substituent in R indicates the position of the substituent on a benzene ring.

Examples 2 to 15

Compounds 2 to 15 shown in the following Table 1 were synthesized by the same method as that of Example 1.

Meanwhile, (R,R)-3,4-diaminohexane used in Examples 14 and 15 was obtained by diaminating (S,S)-3,4-dihydroxyhexane (such as Tetrahedron Letters, 1991, 32, 883) in accordance with the amination method described in a literature (Tetrahedron Asymmetry, 1999, 10, 3559).

TABLE 1

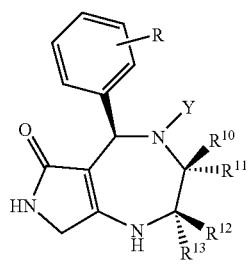
(XII)

| No. | R | —Y | R¹⁰ | R¹¹ | R¹² | R¹³ | D |
|---|---|---|---|---|---|---|---|
| 1 | 2-OMe | COMe | H | Me | Me | H | N1: 0.95(3H, d, J=6.9 Hz), 0.96(3H, d, J=6.0 Hz), 2.13(3H, s), 2.86-2.98(1H, m), 3.75(1H, d, J=16.5 Hz), 3.83(3H, s), 3.84(1H, d, J=16.5 Hz), 3.91-4.03(1H, m), 5.70(1H, s), 6.61(1H, s), 6.78(1H, s), 6.83-7.06(3H, m), 7.23-7.31(1H, m). MS: 330(M+H)+ |
| 2 | 2-OMe | COCH₂OH | H | Me | Me | H | N1: 0.99(3H, d, J=6.0 Hz), 1.02(3H, d, J=6.0 Hz), 2.92-3.04(1H, m), 3.76(1H, d, 15 Hz), 3.81(3H, s), 3.84(1H, d, 15.0 Hz), 3.86-4.01(2H, m), 4.28(1H, t, J=6.0 Hz), 4.48(1H, dd, J=15.0&6.0 Hz), 5.46(1H, s), 6.69(1H, s), 6.82(1H, s), 6.85-7.06(3H, m), 7.25-7.33(1H, m). MS: 346(M+H)+ |
| 3 | 2-OMe | COEt | H | Me | Me | H | N1: 0.92-1.04(9H, m), 2.24-2.40(1H, m), 2.59-2.74(1H, m), 2.87-3.01(1H, m), 3.75(1H, d, 16.0 Hz), 3.83(1H, d, 16.0 Hz), 3.91-4.03(1H, m), 5.78(1H, s), 6.59(1H, s), 6.77(1H, s), 6.82-7.05(3H, m), 7.23-7.31(1H, m). MS: 344(M+H)+ |
| 4 | 2-SMe | COMe | H | Me | Me | H | N1: 0.94(3H, d, J=6.0 Hz), 1.04(3H, d, J=6.9 Hz), 2.19(3H, s), 2.51(3H, s), 3.78(1H, d, J=16.0 Hz), 3.88(1H, d, J=16.0 Hz), 3.90-4.03(1H, m), 5.45(1H, s), 6.66(1H, s), 6.84(1H, s), 6.96-7.01(1H, m), 7.08-7.15(1H, m), 7.27-7.41(2H, m). MS: 346(M+H)+ |
| 5 | 2-SMe | COCH₂OH | H | Me | Me | H | N1: 0.97(3H, d, J=6.3 Hz), 1.11(3H, d, J=7.2 Hz), 2.51(3H, s), 2.74-2.88(1H, m), 3.71-4.01(4H, m), 4.40(1H, t, J=6.0 Hz), 4.78(1H, dd, J=15.6&5.4 Hz), 5.32(1H, s), 6.74(1H, s), 6.89(1H, s), 6.96-7.18(2H, m), 7.29-7.41(2H, m). MS: 362(M+H)+ |
| 6 | 2-cyclopropyl | COCH₂OH | H | Me | Me | H | N1: 0.55-1.05(4H, m), 0.99(3H, d, J=6.6 Hz), 1.10(3H, d, J=6.6 Hz), 1.95-2.02(1H, m), 2.90-3.05(1H m), 3.78(1H, d, J=16.5 Hz), 3.80-3.90(1H, m), 3.89(1H, d, J=16.5 Hz), 3.95-4.05(1H, m), 4.40-4.55(2H, m), 5.68(1H, s), 6.69(1H, s), 6.88(1H, s), 6.96-7.26(4H, m). MS: 356(M+H)+ |
| 7 | 2-OMe | COCH₂CH₂-thiazole | H | Me | Me | H | N1: 0.99(6H, d, J=6.9 Hz), 2.68-3.37(5H, m), 3.76(3H, s), 3.77(1H, d, J=16.0 Hz), 3.86(1H, d, J=16.0 Hz), 3.92-4.05(1H, m), 5.82(1H, s), 6.65(1H, s), 6.80(1H, s), 6.86-7.06(3H, m), 7.25-7.33(1H, m), 7.54(1H, d, J=2.7 Hz), 7.68(1H, d, J=2.7 Hz). MS: 427(M+H)+ |

TABLE 1-continued (XII)

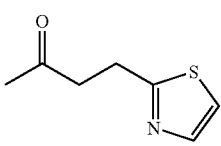

| No. | R | —Y | R10 | R11 | R12 | R13 | D |
|---|---|---|---|---|---|---|---|
| 8 | H | 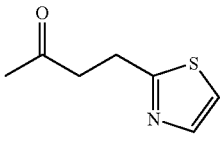 | H | Me | Me | H | N1: 0.96(3H, d, J=6.9 Hz), 1.09(3H, d, J=6.9 Hz), 2.65-3.40(5H, m), 3.76(1H, d, J=16.5 Hz), 3.86(1H, d, J=16.5 Hz), 3.90-4.05(1H, m), 5.71(1H, s), 6.67(1H, s), 6.86(1H, s), 7.16-7.38(5H, m), 7.54(1H, d, J=3.3 Hz), 7.66(1H, d, J=3.3 Hz). MS: 397(M+H)+. |
| 9 | 2-Me | 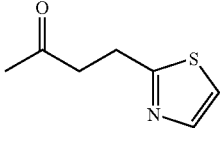 | H | Me | Me | H | N1: 0.95(3H, d, J=6.3 Hz), 1.02(3H, d, J=6.3 Hz), 2.34(3H, s), 2.65-3.25(5H, m), 3.75(1H, d, J=16.5 Hz), 3.88(1H, d, J=16.5 Hz), 3.95-4.05(1H, m), 5.65(1H, s), 6.64(1H, s), 6.83(1H, s), 6.96-7.24(4H, m), 7.52(1H, d, J=3.3 Hz), 7.65(1H, d, J=3.3 Hz). MS: 411(M+H)+ |
| 10 | 2-OCF3 | 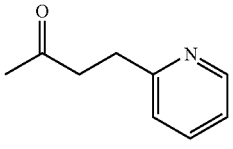 | H | Me | Me | H | N1: 1.00(3H, d, J=6.9 Hz), 1.04(3H, d, J=6.9 Hz), 2.70-3.25(5H, m), 3.77(1H, d, J=16.5 Hz), 3.88(1H, d, J=16.5 Hz), 3.95-4.05(1H, m), 5.83(1H, s), 6.78(1H, s), 6.90(1H, s), 7.16-7.50(4H, m), 7.52(1H, d, J=3.3 Hz), 7.65(1H, d, J=3.3 Hz). MS: 481(M+H)+ |
| 11 | 2-OMe | 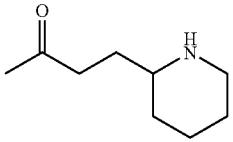 | H | Me | Me | H | N1: 0.97(6H, d, J=6.9 Hz), 2.65-3.25(5H, m), 3.76(1H, d, J=16.0 Hz), 3.79(3H, s), 3.83(1H, d, J=16.0 Hz), 3.91-4.02(1H, m), 5.82(1H, s), 6.62(1H, s), 6.77(1H, s), 6.84-7.04(3H, m), 7.14-7.31(3H, m), 7.66(1H, dt, J=7.5&1.8 Hz), 8.44-8.50(1H, m). MS: 421(M+H)+ |
| 12 | 2-OMe | 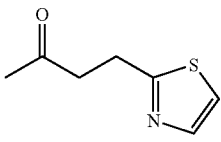 | H | Me | Me | H | N1: 0.90-3.50(15H, m), 3.74(1H, d, J=16.0 Hz), 3.83(3H, s), 3.84(1H, d, J=16.0 Hz), 3.90-4.04(1H, m), 5.80(1H, s), 6.65(1H, s), 6.79(1H, s), 6.84-7.06(3H, m), 7.23-7.32(1H, m). MS: 427(M+H)+ |
| 13 | 2-OMe | 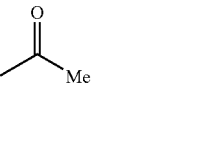 | H | H | H | H | N1: 2.50-3.95(10H, m), 3.77(3H, s), 6.06(1H, br s), 6.76-7.05(5H, m), 7.28(1H, t, J=6.9 Hz), 7.55(1H, m), 7.68(1H, m). MS: 399(M+H)+ |
| 14 | 2-OMe |  | H | Et | Et | H | N1: 7.30-7.40(1H, m), 6.9-7.1(3H, m), 6.4-6.5(1H, brs), 6.09-6.18(1H, brs), 3.90-4.22(3H, m), 3.89(3H, s), 3.15-3.40(2H, m), 2.34(3H, s), 2.08-2.28(1H, m), 1.50-1.75(2H, m), 1.12-1.30(1H, m), 0.86(3H, t, J=7.5), 0.15(3H, t, J=7.5). MS: 358(M |

TABLE 1-continued

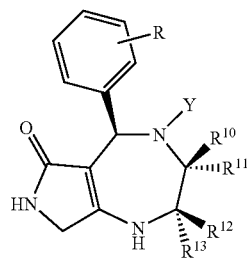

(XII)

| No. | R | —Y | $R^{10}$ | $R^{11}$ | $R^{12}$ | $R^{13}$ | D |
|---|---|---|---|---|---|---|---|
| 15 | 2-OMe | ![O, OH ketone-alcohol] | H | Et | Et | H | N1: 7.26-7.38(1H, m), 6.88-7.04(3H, m), 6.79(1H, s), 6.45(1H, s), 5.57(1H, s), 4.45-4.70(2H, m), 4.25-4.35(1H, brs), 3.90-4.00(2H, m), 3.81(3H, s), 2.98-3.10(1H, m), 2.05-2.20(2H, m), 1.50-1.65(1H, m), 1.00-1.20(1H, m), 0.78(3H, t, J=7.5), |

Example 16

Evaluation of the Sugar Transporting Capacity

1. Preparation of Adipose Cells of Rats:

After the decapitation and venesection of 6 male Wistar rats (body weight: 150 to 200 g), an incision was made in the abdomen of each rat to extract 6 g in total of epididymal adipose tissues. The tissues were finely cut into 2 mm×2 mm pieces in 6 ml of KRH (Krebs-Ringer Hepes, composition: 130 mM of sodium chloride, 4.7 mM of potassium chloride, 1.2 mM of potassium dihydrogenphosphate, 1.2 mM of magnesium sulfate, 1 mM of calcium chloride and 25 mM of Hepes, pH=7.6) containing 5% of BSA (bovine serum albumin). 24 mg of collagenase (type I) was added thereto and the digestion treatment was conducted for about 40 minutes to obtain about 6 ml of isolated adipose cells. The collagenase was removed by the buffer exchange. 2% BSA/KRH solution was added to the residue for the re-suspension to obtain 45 ml of an adipose cell suspension.

2. Evaluation of the Sugar Transporting Capacity:

The sugar transporting capacity of the compound of the present invention was evaluated with reference to a method described in a literature [Annual Review of Biochemistry, Vol. 55, p. 1059 (1986)]. In the test, 200 μL of the adipose cell suspension was poured in each polystyrene test tube, 100 μL of the solution of the test substance (by dilution of 10 mg/mL dimethyl sulfoxide solution with KRH) was added thereto, and the obtained mixture was shaken and then cultured at 37° C. for 30 minutes.

The sugar transporting capacity was evaluated by measuring the quantity of 2-[$^{14}$C(U)]-deoxy-D-glucose incorporated per a unit time. Namely, 2-[$^{14}$C(U)]-deoxy-D-glucose was added to the adipose cell suspension after the pre-culture (the final concentration: 0.5 μCi/sample). 5 minutes later, cytochalasin B (final concentration: 10 μM) was added to the mixture to terminate the sugar transportation. After forming a dinonyl phthalate layer, the obtained mixture was centrifuged to separate the adipose cells from the buffer. The quantity of 2-[$^{14}$C(U)]-deoxy-D-glucose contained in the adipose cell layer was determined with a liquid scintillation counter to determine the quantity of the incorporated sugar. In this evaluation system, when insulin (100 nM) having the effect of increasing the sugar-transporting capacity was used, the effect was about 7 times as high as that obtained in the insulin-free control group.

The results of the evaluation of the sugar-transporting capacity obtained by using the compounds of the present invention are shown in Table 2. The sugar-transporting capacity in Table 2 was determined in terms of the concentration ($EC_{50}$: μg/mL) of a test compound, having a reinforcing effect corresponding to 50% on the basis of the reinforcing effect of insulin (100 nM). (The symbols in Table 2 are as follows: No: Example No., and A: sugar-transporting capacity.)

TABLE 2

| No. | A |
|---|---|
| 3 | 6.0 |
| 7 | 0.06 |
| 8 | 0.31 |
| 9 | 0.15 |
| 10 | 0.2 |
| 11 | <0.1 |

What is claimed is:

1. A fused polycyclic compound of formula (I) or a pharmaceutically acceptable salt thereof:

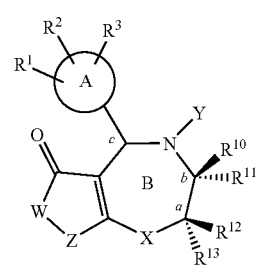

(I)

wherein:

A represents an aromatic cyclic group, heterocyclic group or aliphatic cyclic group;

$R^1$, $R^2$ and $R^3$ may be same or different from each other and each independently represent a hydrogen atom, halogen atom, hydroxyl group, mercapto group, alkoxy group, alkylthio group, alkylsulfonyl group, acyl group, acyloxy group, amino group, alkylamino group, carboxyl group, alkoxycarbonyl group, carbamoyl group, nitro group, cyano group, trifluoromethyl group, alkyl group which may have a substituent(s), alkenyl group which may have a substituent(s), alkynyl group which may have a substituent(s), aryl group which may have a substituent(s), heteroaryl group which may have a substituent(s), benzyloxy group which may have a substituent(s), aryloxy group which may have a substituent(s), heteroaryloxy group which may have a substituent(s), arylamino group which may have a substituent(s), arylvinyl group which may have a substituent(s) or arylethynyl group which may have a substituent(s);

—Z— represents —O—, —NH—, —NR$^6$—, —S—, —SO—, —SO$_2$—, —CH$_2$—, —CR$^4$R$^5$— or —CO—, wherein R$^6$ represents a lower alkyl group which may have a substituent(s), acyl group which may have a substituent(s), alkoxycarbonyl group which may have a substituent(s), carbamoyl group which may have a substituent(s) or sulfonyl group which may have a substituent(s), R$^4$ and R$^5$ may be same or different from each other and each independently represent a hydrogen atom, halogen atom, hydroxyl group, alkyl group, mercapto group, alkoxy group, alkylthio group, alkylsulfonyl group, acyl group, acyloxy group, amino group, alkylamino group, carboxyl group, alkoxycarbonyl group, carbamoyl group, nitro group, cyano group or trifluoromethyl group;

—X— represents —NH— or —NR$^6$—;

—W— represents —NR$^9$—, —O— or —CR$^7$R$^8$—, wherein R$^9$ represents a hydrogen atom, lower alkyl group which may have a substituent(s) or aryl group which may have a substituent(s), R$^7$ and R$^8$ may be same or different from each other and each independently represent a hydrogen atom, halogen atom, hydroxyl group, alkyl group, mercapto group, alkoxy group, alkylthio group, alkylsulfonyl group, acyl group, acyloxy group, amino group, alkylamino group, carboxyl group, alkoxycarbonyl group, carbamoyl group, nitro group, cyano group or trifluoromethyl group;

Y represents a lower alkyl group which may have a substituent(s), acyl group which may have a substituent(s), alkoxycarbonyl group which may have a substituent(s), carbamoyl group which may have a substituent(s) or sulfonyl group which may have a substituent(s);

R$^{10}$, R$^{11}$, R$^{12}$ and R$^{13}$ may be same or different from each other and each independently represent a hydrogen atom, halogen atom, lower alkyl group which may have a substituent(s), lower alkenyl group which may have a substituent(s), lower alkynyl group which may have a substituent(s), aryl group which may have a substituent(s), heteroaryl group which may have a substituent(s), carboxyl group, alkoxycarbonyl group, carbamoyl group or cyano group; and a, b and c represent a position of a carbon atom, respectively;

with the proviso that (i) the above substituent(s) is selected from the group consisting of a halogen atom, hydroxyl group, alkyl group, mercapto group, alkoxy group, alkylthio group, alkylsulfonyl group, acyl group, acyloxy group, amino group, alkylamino group, carboxyl group, alkoxycarbonyl group, carbamoyl group, nitro group, cyano group, trifluoromethyl group, aryl group and heteroaryl group; and (ii) two or more of R$^{10}$, R$^{11}$, R$^{12}$ and R$^{13}$ do not form a ring together.

2. The fused polycyclic compound or pharmaceutically acceptable salt thereof according to claim 1, wherein A represents an aromatic cyclic group or heterocyclic group; —Z— represents —CH$_2$— or —CR$^4$R$^5$—; —W— represents —NR$^9$—; Y represents an acyl group which may have a substituent(s), alkoxycarbonyl group which may have a substituent(s) or carbamoyl group which may have a substituent(s); either one or both of R$^{10}$ and R$^{11}$ is a hydrogen atom; and either one or both of R$^{12}$ and R$^{13}$ is a hydrogen atom.

3. The fused polycyclic compound or pharmaceutically acceptable salt thereof according to claim 2, wherein Y is an acyl group which may have a substituent(s) and is represented by formula (II):

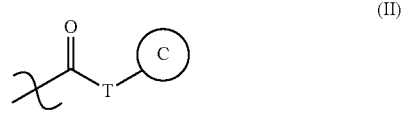

(II)

wherein two carbon atoms in T may have a double bond or triple bond, some of the carbon atom(s) in the group may be substituted with an oxygen, sulfur or nitrogen atom, and T represents an alkylene group having 1 to 7 carbon atoms; and C represents an aromatic cyclic group or heterocyclic group which may have a substituent(s).

4. The fused polycyclic compound or pharmaceutically acceptable salt thereof according to claim 2, wherein Y is an acyl group which may have a substituent(s) and is represented by formula (II):

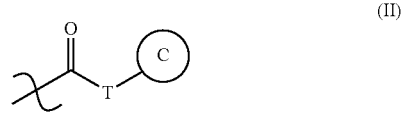

(II)

wherein C represents a furyl group which may have a substituent(s), thienyl group which may have a substituent(s), oxazolyl group which may have a substituent(s), isoxazolyl group which may have a substituent(s), thiazolyl group which may have a substituent(s), oxadiazolyl group which may have a substituent(s), thiadiazolyl group which may have a substituent(s), pyridyl group which may have a substituent(s), piperidyl group which may have a substituent(s), pyridonyl group which may have a substituent(s), pyridazinyl group which may have a substituent(s), pyrimidinyl group which may have a substituent(s), imidazolyl group which may have a substituent(s), or 4-oxothiazolidine-2-thionyl group which may have a substituent(s); and -T- represents —CH$_2$— or —CH$_2$CH$_2$—.

5. The fused polycyclic compound or pharmaceutically acceptable salt thereof according to claim 4, wherein C represents a furyl group, thienyl group, oxazolyl group, isoxazolyl group, thiazolyl group, oxadiazolyl group, pyridyl group, piperidyl group, pyridazinyl group, or pyrimidinyl group.

6. The fused polycyclic compound or pharmaceutically acceptable salt thereof according to claim 2, wherein Y represents an unsubstituted acyl group or an acyl group which has an alkyl group(s) with 1 to 6 carbon atoms having a hydroxyl group as a substituent.

7. The fused polycyclic compound or pharmaceutically acceptable salt thereof according to claim 2, wherein A is a phenyl group; —X— represents —NH— or —NMe-; W is —NH—; both $R^{10}$ and $R^{13}$ are hydrogen atoms; and $R^{11}$ and $R^{12}$ may be same or different from each other and each independently represent a hydrogen atom, lower alkyl group which may have a substituent(s), lower alkenyl group which may have a substituent(s), or lower alkynyl group which may have a substituent(s).

8. The fused polycyclic compound or pharmaceutically acceptable salt thereof according to claim 2, wherein all of $R^1$, $R^2$ and $R^3$ are hydrogen atoms, or two of $R^1$, $R^2$ and $R^3$ are hydrogen atoms and one of $R^1$, $R^2$ and $R^3$ is an alkoxy group, alkylthio group, alkylsulfonyl group, acyl group, acyloxy group, amino group, alkylamino group, alkoxycarbonyl group, carbamoyl group, trifluoromethyl group, alkyl group which may have a substituent(s), alkenyl group which may have a substituent(s), or alkynyl group which may have a substituent(s).

9. The fused polycyclic compound or pharmaceutically acceptable salt thereof according to claim 8, wherein all of $R^1$, $R^2$ and $R^3$ are hydrogen atoms, or two in $R^1$, $R^2$ and $R^3$ are hydrogen atoms and one of $R^1$, $R^2$ and $R^3$ is an alkoxy group having 1 to 18 carbon atoms, alkylthio group having 1 to 12 carbon atoms, alkylsulfonyl group having 1 to 12 carbon atoms, trifluoromethyl group, or alkyl group having 1 to 18 carbon atoms.

10. The fused polycyclic compound or pharmaceutically acceptable salt thereof according to claim 7, wherein $R^{11}$ and $R^{12}$ may be same or different from each other and each independently represent a lower alkyl group which may have a substituent(s), lower alkenyl group which may have a substituent(s), or lower alkynyl group which may have a substituent(s).

11. The fused polycyclic compound or pharmaceutically acceptable salt thereof according to claim 10, wherein $R^{11}$ and $R^{12}$ may be same or different from each other and each independently represent a lower alkyl group which may have a substituent(s).

12. A pharmaceutical composition, which comprises a fused polycyclic compound or pharmaceutically acceptable salt thereof according to claim 1 and one or more pharmaceutically acceptable excipients.

13. A pharmaceutical composition, which comprises a fused polycyclic compound or pharmaceutically acceptable salt thereof according to claim 2 and one or more pharmaceutically acceptable excipients.

14. A pharmaceutical composition, which comprises a fused polycyclic compound or pharmaceutically acceptable salt thereof according to claim 3 and one or more pharmaceutically acceptable excipients.

15. A pharmaceutical composition, which comprises a fused polycyclic compound or pharmaceutically acceptable salt thereof according to claim 4 and one or more pharmaceutically acceptable excipients.

16. A pharmaceutical composition, which comprises a fused polycyclic compound or pharmaceutically acceptable salt thereof according to claim 5 and one or more pharmaceutically acceptable excipients.

17. A pharmaceutical composition, which comprises a fused polycyclic compound or pharmaceutically acceptable salt thereof according to claim 6 and one or more pharmaceutically acceptable excipients.

18. A pharmaceutical composition, which comprises a fused polycyclic compound or pharmaceutically acceptable salt thereof according to claim 7 and one or more pharmaceutically acceptable excipients.

19. A pharmaceutical composition, which comprises a fused polycyclic compound or pharmaceutically acceptable salt thereof according to claim 8 and one or more pharmaceutically acceptable excipients.

20. A pharmaceutical composition, which comprises a fused polycyclic compound or pharmaceutically acceptable salt thereof according to claim 9 and one or more pharmaceutically acceptable excipients.

* * * * *